United States Patent
Sughrue et al.

(10) Patent No.: US 11,042,971 B1
(45) Date of Patent: Jun. 22, 2021

(54) MEDICAL IMAGING WITH DISTORTION CORRECTION

(71) Applicant: Omniscient Neurotechnology Pty Limited, Sydney (AU)

(72) Inventors: Michael Edward Sughrue, Sydney (AU); Stephane Philippe Doyen, Glebe (AU); Peter James Nicholas, South Hurstville (AU)

(73) Assignee: Omniscient Neurotechnology Pty Limited, Sydney (AU)

( * ) Notice: Subject to any disclaimer, the term of this patent is extended or adjusted under 35 U.S.C. 154(b) by 0 days.

(21) Appl. No.: 16/993,011

(22) Filed: Aug. 13, 2020

(51) Int. Cl.
*G06K 9/00* (2006.01)
*G06T 5/00* (2006.01)
(Continued)

(52) U.S. Cl.
CPC ............ *G06T 5/006* (2013.01); *A61B 5/0042* (2013.01); *A61B 5/055* (2013.01);
(Continued)

(58) Field of Classification Search
CPC ........... G06T 19/20; G06T 2207/10028; G06T 7/0012; G06T 7/33; G06T 2207/10088; G06T 2219/2004; G06T 19/006; G06T 2207/20081; G06T 7/30; G06T 7/344; G06T 7/38; G06T 2207/10016; G06T 2207/10024; G06T 2207/10081; G06T 5/50; G06T 7/11; G06T 7/32;
(Continued)

(56) References Cited

U.S. PATENT DOCUMENTS

2003/0088177 A1* 5/2003 Totterman ............. G06T 7/0016 600/414
2003/0216631 A1* 11/2003 Bloch ....................... G06T 7/33 600/407
(Continued)

OTHER PUBLICATIONS

Becker et al., "Going Beyond Diffusion Tensor Imaging Tractography in Eloquent Glioma Surgery-High-Resolution Fiber Tractography: Q-Ball or Constrained Spherical Deconvolution?" World Neurosurg., Feb. 2020 134:e596-609.
(Continued)

*Primary Examiner* — Alex Kok S Liew
(74) *Attorney, Agent, or Firm* — Fish & Richardson P.C.

(57) ABSTRACT

Methods, systems, and apparatus, including computer programs encoded on computer storage media, for medical imaging with distortion correction. One example includes obtaining distorted image data of a subject brain, the distorted image data comprising a time series of three-dimensional image tensors generated at least in part from an echo planar imaging session of the subject brain. A derived three-dimensional tensor is derived from the distorted image data. A non-rigid alignment function to non-rigidly align the derived three-dimensional tensor to a reference tensor is determined, producing a non-rigidly aligned derived 3D tensor. A rigid alignment function to rigidly align the non-rigidly aligned derived 3D tensor to the reference tensor is determined. Distortion-corrected image data is created by applying the rigid alignment function and the non-rigid alignment function to the time series of three-dimensional image tensors.

24 Claims, 7 Drawing Sheets

(51) Int. Cl.
| | |
|---|---|
| G06T 5/50 | (2006.01) |
| G06T 7/00 | (2017.01) |
| A61B 5/055 | (2006.01) |
| A61B 5/00 | (2006.01) |
| G01R 33/48 | (2006.01) |
| G01R 33/563 | (2006.01) |
| G01R 33/561 | (2006.01) |
| G01R 33/56 | (2006.01) |
| G01R 33/565 | (2006.01) |

(52) U.S. Cl.
CPC ..... *G01R 33/4806* (2013.01); *G01R 33/5608* (2013.01); *G01R 33/5616* (2013.01); *G01R 33/56341* (2013.01); *G01R 33/56554* (2013.01); *G06T 5/50* (2013.01); *G06T 7/0012* (2013.01); *G06T 2207/10092* (2013.01); *G06T 2207/20216* (2013.01); *G06T 2207/30016* (2013.01)

(58) Field of Classification Search
CPC . G06T 2200/04; G06T 2200/08; G06F 30/20; G06F 17/10; G06F 30/00; G06F 3/011; G06F 3/017; G06F 3/0304; G06F 3/0346
See application file for complete search history.

(56) References Cited

U.S. PATENT DOCUMENTS

| | | | | |
|---|---|---|---|---|
| 2008/0009683 | A1* | 1/2008 | Bogoni | A61B 5/085 600/300 |
| 2014/0037161 | A1* | 2/2014 | Rucker | A61B 5/0033 382/128 |

OTHER PUBLICATIONS

Bhushan et al., "Correcting Susceptibility-Induced Distortion in Diffusion-Weighted MRI using Constrained Nonrigid Registration," Signal Inf. Process Assoc. Annu. Summit Conf. APSIPA Asia Pac, Dec. 2012, 1-9.

Bonney et al., A Simplified Method of Accurate Postprocessing of Diffusion Tensor Imaging for Use in Brain Tumor Resection. Oper Neurosurg (Hagerstown) 13, 47-59 (2017).

Burks et al., "A method for safely resecting anterior butterfly gliomas: the surgical anatomy of the default mode network and the relevance of its preservation". J. Neurosurg., Sep. 2016, 126(6):1795-811.

Dell'Acqua and Tournier, "Modelling white matter with spherical deconvolution: How and why?" NMR Biomed., 2019, 32:e3945.

Fan et al., "The Human Brainnetome Atlas: A New Brain Atlas Based on Connectional Architecture," Cereb Cortex, 2016, 26:3508-26.

Fischl, "FreeSurfer," Neuroimage, 2012, 62:774-81.

Garyfallidis et al., "Dipy, a library for the analysis of diffusion MRI data," Frontiers in Neuroinformatics, 2014, 8:1-17.

Glasser et al., "A multi-modal parcellation of human cerebral cortex," Nature, 2016, 536:171-8.

Glenn et al., "Common Disconnections in Glioma Surgery: An Anatomic Description," Cureus, 2017, 9:e1778.

Ille et al., Functional Reorganization of Cortical Language Function in Glioma Patients—A Preliminary Study. Frontiers in Oncology 9 (2019).

Jin et al., "Functional and anatomical connectivity-based parcellation of human cingulate cortex." Brain Behav., 2018, 8:e01070.

Ohue et al., "Evaluation of intraoperative brain shift using an ultrasound-linked navigation system for brain tumor surgery," Neurol. Med. Chir., 2010, 50:291-300.

Panesar et al., "Tractography for Surgical Neuro-Oncology Planning: Towards a Gold Standard," Neurotherapeutics, 2019, 16:36-51.

Poynton et al., "Fieldmap-Free Retrospective Registration and Distortion Correction for EPI-Based Functional Imaging," Med. Image Comput. Comput. Assit. Interv., Sep., 2008, 11(Pt2):271-9.

Rijnen et al., "Cognitive functioning in patients with low-grade glioma: effects of hemispheric tumor location and surgical procedure" 2019, 1(4):81-99.

Smitha et al., "Resting state fMRI: A review on methods in resting state connectivity analysis and resting state networks," Neuroradiol. J., 2017, 30:305-17.

Song et al., "A Review of Methods for Bias Correction in Medical Images," Biomedical Engineering Review, Sep. 2017, 1(1):1-10.

* cited by examiner

MEDICAL IMAGING WITH DISTORTION CORRECTION

TECHNICAL FIELD

This document describes medical imaging technology.

BACKGROUND

Medical imaging includes the technique and process of creating visual representations of the interior of a body for clinical analysis and medical intervention, as well as visual representation of the function of some organs or tissues (physiology). Medical imaging seeks to reveal internal structures hidden by the skin and bones, as well as to diagnose and treat disease. Medical imaging also establishes a database of normal anatomy and physiology to make it possible to identify abnormalities.

SUMMARY

Technology described in this document can be used for generating an image. In one implementation, a method includes obtaining distorted image data of a subject brain, the distorted image data comprising a time series of three-dimensional image tensors generated at least in part from an echo planar imaging session of the subject brain. The method includes deriving a derived three-dimensional tensor from the distorted image data. The method includes determining a non-rigid alignment function to non-rigidly align the derived three-dimensional tensor to a reference tensor producing a non-rigidly aligned derived 3D tensor. The method includes determining a rigid alignment function to rigidly align the non-rigidly aligned derived 3D tensor to the reference tensor. The method includes producing distortion-corrected image data by applying the rigid alignment function and the non-rigid alignment function to the time series of three-dimensional image tensors. Other implementations can include devices, software, computer-readable media, and products.

Implementations can include all, some, or none of the following features. Determining the rigid alignment function comprises selecting a portion of the derived three-dimensional tensor as an anchor; finding a target-portion of the reference tensor that corresponds to the anchor; and finding a translation of the anchor that minimizes a different function between the anchor and the target portion. Selecting a portion of the derived three-dimensional tensor as an anchor can include finding a center of the derived three-dimensional tensor. Determining the non-rigid alignment function can include determining an affine transformation that specifies the difference in shape between the derived three-dimensional tensor to the reference tensor. The transformation, when applied to the distorted image data, can transform a first portion of the distorted image data and not transform a second portion of the distorted image data. Deriving a derived three-dimensional tensor from the distorted image data can include averaging voxel values of each address location across a plurality of volumetric images of the distorted image data. The method can further include one or more of i) displaying the distortion-corrected image data to a user; ii) storing the distortion-corrected image data; and iii) performing clinical analysis for the patient using the distortion-corrected image to produce a result different than what would be produced performing the clinical analysis on the volumetric image data. The echo planar imaging session of the subject brain can be free of a sensing for generation of a field gradient map and the producing of the image data can be performed free of a field gradient map. The echo planar imaging can be one of the group consisting of functional magnetic resonance (fMRI) and imaging and diffusion tractography (DT). The reference tensor can represent a T1 image.

Implementations can provide all, some, or none of the following advantages. The technology of medical imaging is advanced. Volumetric imaging data that is distorted can be corrected to reduce or eliminate the distortion. This correction can be completed without the generation or use of a gradient field map, which can require more time and complexity than what is required by this technology.

DESCRIPTION OF DRAWINGS

Like reference symbols in the various drawings indicate like elements.

DETAILED DESCRIPTION

Described here is technology for generating images with reduced or removed distortions. For example, echo planar imaging of a subject brain may be distorted in the orbital-frontal area caused by air of the subject's sinus cavity. This technology can use a T1 image as a reference tensor to represent a target shape. Then, a non-rigid alinement and a rigid alinement can be applied to the distorted data to match the target tensor.

Figure 1:
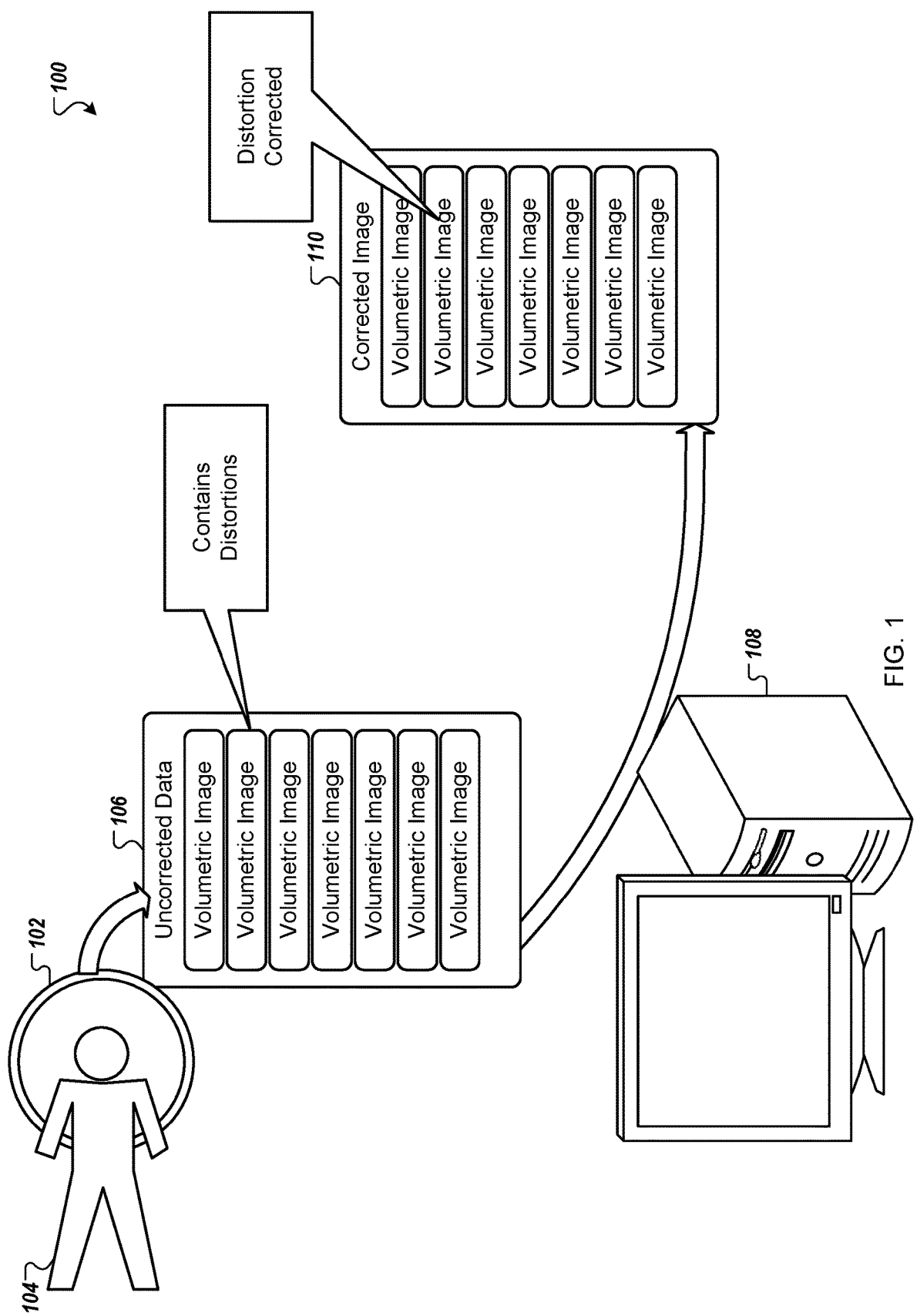
FIG. 1 shows an example system for generating medical images with distortion correction.

FIG. 1 shows an example system 100 for generating medical images with distortion correction. In the system 100, a medical imager 102 images a patient 104 to generate uncorrected data 106 for a clinical-data client 108. The client 108 prepares, from the data 106, a corrected image 110 by correcting distortions that are contained in the uncorrected data 106. The resulting corrected image series 110 may then be used for an array of clinical uses such as diagnostic analysis, surgery planning, automated analysis, etc.

When the medical imager 102 generates uncorrected data 106, the air in the sinus cavity of the patient 104 influences the values stored in the data. This influence can result in a corresponding areas in the uncorrected data 106 recording values, that when rendered, would render a shape different from that of the brain being imaged. As such, the uncorrected data 106 may be of lower value for diagnostic or other purposes than if the distortions where corrected as in the corrected image 110.

When subjecting the uncorrected data 106 to analysis, such distorted data may produce anomalous results ranging from a reduction in accuracy and/or completely incorrect results. As such, the client 108 may apply one or more distortion correction techniques to the uncorrected data 106 in order to produce a corrected image series 110. For example, by using a T1 image that is not subject to the same distortions as other sensing/imaging techniques (e.g., the echo planar imaging (EPI) sequences such as DTI and fMRI), the client 108 can transform and translate the volumetric images of the uncorrected data 106 to match or be more similar to the shape of the target. As such, the creation of the image 110 represents an improvement in the technology of volumetric sensing in that superior-accuracy images 110 can be produced compared to lower-accuracy data 106.

The medical imager 102 represents any sort of device that generates medical images, including DICOM or similar images. Examples include MRI machines, computed tomography machines, X-Ray machines, and ultrasound machines, which can be used in fields including, but not limited to, radiology, cardiology, oncology, nuclear medicine, radiotherapy, neurology, orthopedics, obstetrics, gynecology, ophthalmology, dentistry, maxillofacial surgery, dermatology, pathology, clinical trials, veterinary medicine, and medical/clinical photography.

The clinical-data client 108 represents a computing device that provides a user with interface elements to manipulate data, including the uploading of imaging data to a cloud-service provider 112. This can include laptop or desktop computers, workstations, servers, telephone devices, tablet devices, control-panels attached to or incorporated with the medical imager 102.

Figure 2:
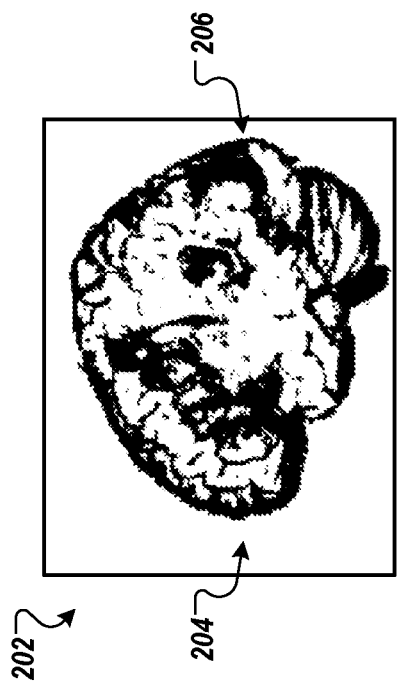
FIG. 2 shows an example of distortion correction applied to a medical image.
Figure 2:

FIG. 2 shows an example of distortion correction applied to a medical image. Rendering 200 shows the uncorrected data 106 rendered into a two dimensional (2D) image, and rendering 202 shows the corrected image 110 rendered into a 2D image. However, it will be understood that, as the data 106 and image 110 are four dimensional (4D), other renderings are possible, and that some detail is lost when projecting 4D to 2D.

The renderings 200 and 202 include an area 204. In the rendering 200, a distortion of the patient's 104 brain is shown in the area 204. In the rendering 202, the distortion has been corrected in the area 204. The renderings 200 and 202 also include an area 206. In rendering 202, there is no or minimal distortion due to the air in the patient's 104 sinus cavity.

Figure 3:
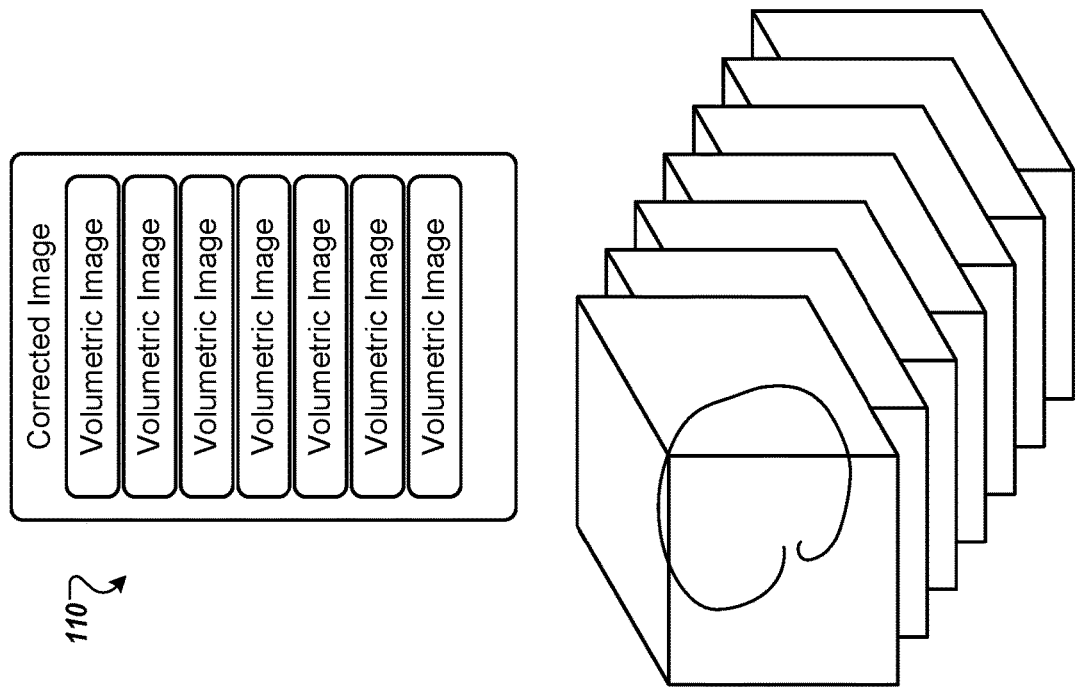
FIG. 3 shows data generated by medical imaging.
Figure 3:
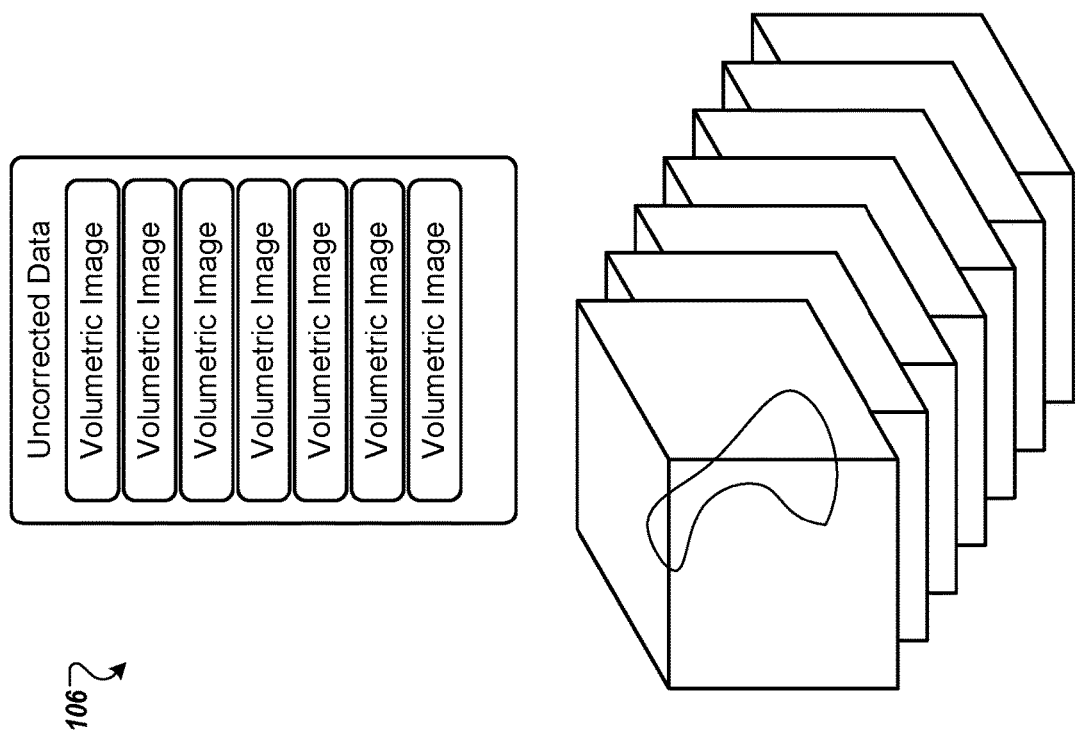

FIG. 3 shows an example of data 106 and an associated image 110 with and without corrections of distortions found in the data 106. In the data 106, each volumetric image generated by the scanner 102 is shown. After the data 106 is processed to remove distortions, the image 110 is created from the volumetric images that are not determined to have the invalid data. As such, the image 110 may have the same number of the volumetric images of the data 106, although more or fewer are possible.

Figure 4:
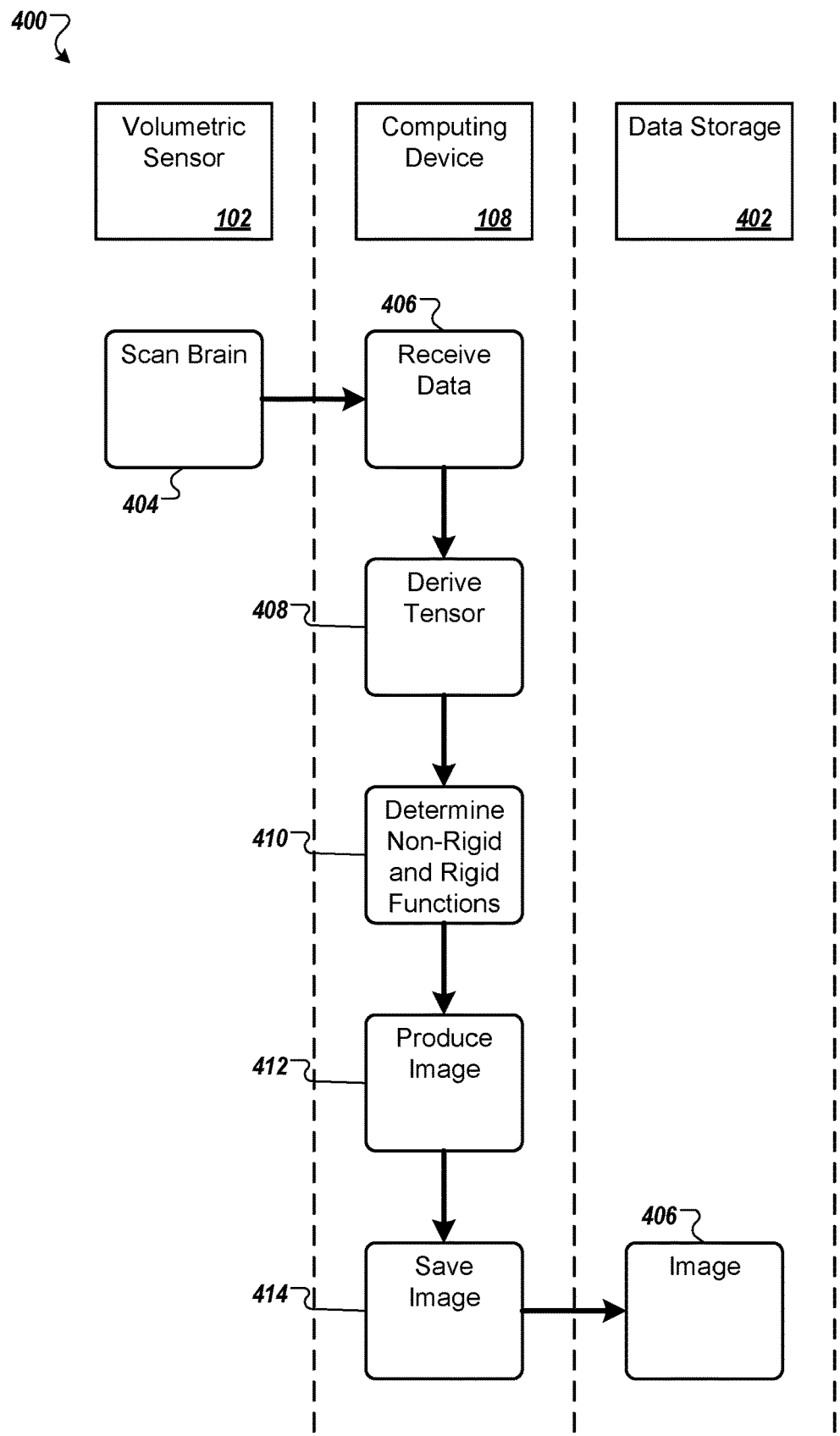
FIGS. 4 and 5 show flowcharts of example processes for generating a medical image.

FIG. 4 shows a flowchart of an example process for generating a medical image. The process 400 may be used, for example, by the client 108 in preparing the image 110, though it may be used for other systems and purposes.

The volumetric sensor 102 scans a brain 404. For example, an MRI machine may record a series of sequential brain scans in order to assist a clinician. These scans may generate data based on using magnetic resonance imaging or other medical imaging technique. In some cases, such a scanning can include, but is not limited to, magnetic resonance imaging such as functional magnetic resonance imaging (fMRI) and diffusion tractography (DT)/diffusion tractography imaging (DTI).

As will be understood, such scans can in some cases record data that has been distorted away from the actual phenomenon being scanned. For example, air in a patient's sinus cavity or other features may cause distortions in the locations, but not intensity, of readings. As will be described, this distorted data can be corrected in the process 400.

This scan 404 can be performed without the need to perform the sensing necessary to generate a field gradient map. Further, the process 400 can be altogether free of a field gradient map. As such, the process 400 can be advantageously performed faster, and with less expense, than other processes that create field gradient maps.

The device 108 receives the data 406. For example, a desktop computer may receive scan data generated by the sensing of a subject brain from the MM machine via an Ethernet data network, and data generated by the MM machine may be transmitted directly to the desktop computer or may be stored in a datastore (e.g., a datastore 402) for access by the desktop computer.

For example, the obtained distorted image data of a subject brain can include a time series of three-dimensional image tensors generated at least in part from an echo planar imaging session of the subject brain. This may take the form of a series of volumetric images in the uncorrected data 106.

The device 108 derives a tensor from the distorted image data 408. For example, each of the volumetric images may be averaged together to create the derived tensor. In order to create the derived tensor, the computing device 108 may first access each voxel value at a given [X,Y,Z] location in each volumetric image. Then, an average for that location can be found by averaging the voxel values accessed. This average voxel value can then be stored in an empty template that has initially-empty voxel locations [X,Y,Z] corresponding to the address space of the volumetric images. Other statistical processes may be used in addition or in the alternative. For example, modal values may be used, outlier voxel values can be excluded, and some (e.g., first and last) volumetric images may be excluded, to name a few.

The device 108 determines a non-rigid alignment function and a rigid alignment function to align the derived 3D tensor to a reference tensor 410 and the device 108 produces a distortion-corrected image 412. One example process for such determinations and productions is described later in the process 500.

The device 108 saves an image 414. For example, the desktop computer can compile the distortion-corrected volumetric images into a new distorting-corrected image. In some cases, this image may be stored as a four dimensional (4D) image, with the four dimensions being X, Y, and Z in space, and T in time, with one volumetric image at each time point T.

The data storage 402 stores the image. The data storage 402 may be local to the desktop (e.g., installed inside a case of the desktop as a hard disk) or network-attached (e.g., a remote server that is in data communication with the desktop).

With the image stored in the data storage 402, the desktop or another computer system or device can access the saved image as a distortion-corrected image that corrects for distorted data created by operation of a magnetic resonance imaging system. For example, a desktop running computer software can be configured to provide data visualization for surgical planning, brain network visualization, anomaly detection in brain activity, and segregation of brain networks.

This may allow for i) the displaying of the distortion-corrected image data to a user; ii) the storing of the distortion-corrected image data; and/or iii) the performing of clinical analysis for the patient using the distortion-corrected image to produce a result different than what would be produced performing the clinical analysis on the volumetric image data.

Figure 5:
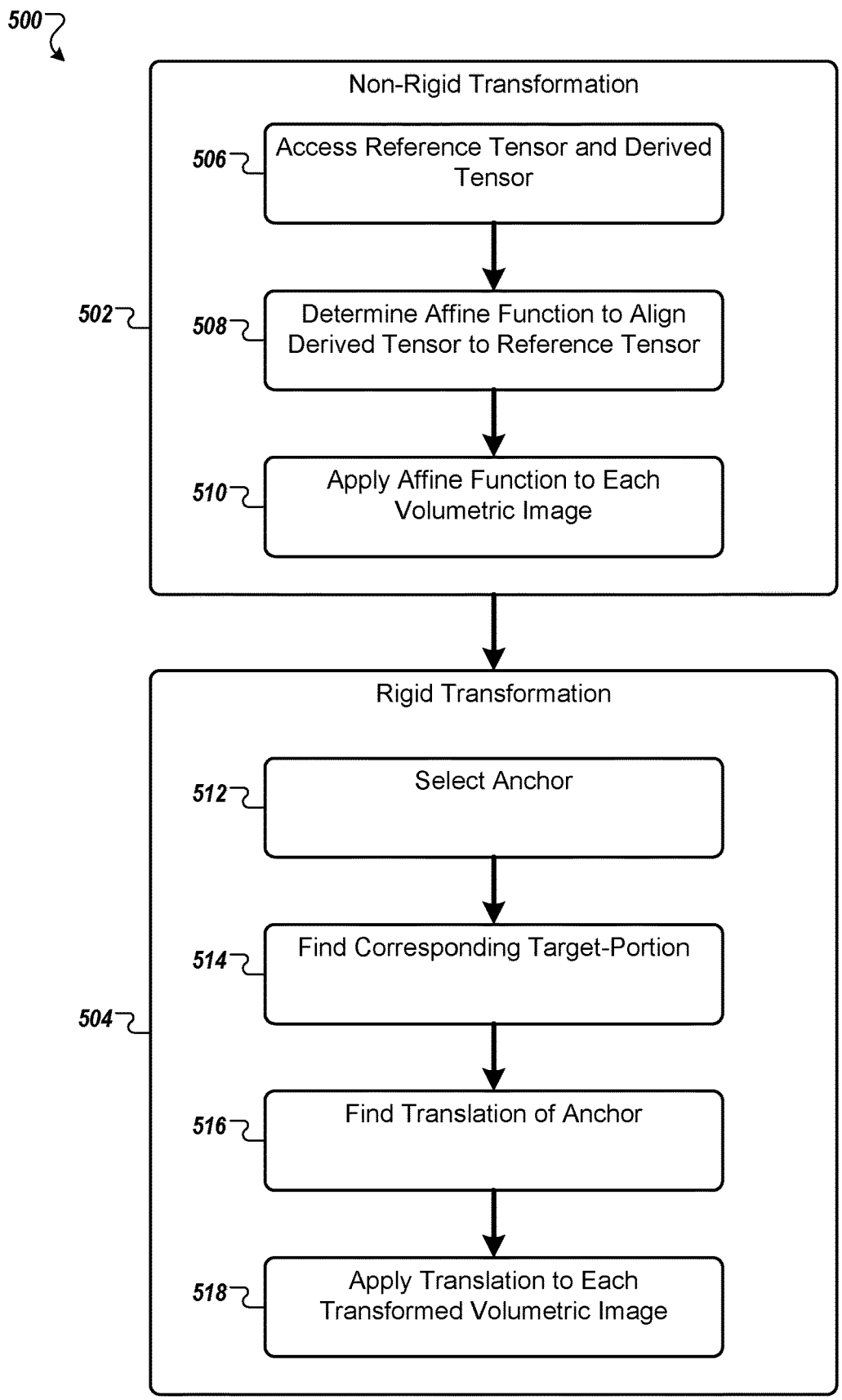

FIG. 5 shows a flowchart of an example process 500 for generating a medical image. The process 500 can be used, for example, to determine a non-rigid alignment function and a rigid alignment function to align the derived 3D tensor to a reference tensor 410 and to produce a distortion-corrected image 412.

In the process 500, a non-rigid transformation 502 is found and applied to each volumetric images of a medical image. In general, this can be understood to change the shape of the brain recorded in the image data. Then, a rigid transformation 504 is found and applied to each of the volumetric images of the medical image. In general, this can be understood as reorienting the re-shaped brain to the correct alignment. In general, the non-rigid transformation 502 is an optimization of the discrepancy of voxel values to a minimum discrepancy value and the rigid transformation 504 is an optimization to minimize the distance between two centers of mass to a minimum.

A reference tensor and derived tensor are accessed 506. For example, the reference tensor created in 408 may be accessed. The reference tensor may be, or may be generated from, an undistorted or minimally-distorted volumetric image of the subjects brain. For example, the reference tensor may be, or may be generated from, a T1 image of the subject brain. As will be appreciated, the scanning to generate the T1 image may take less time and resources compared to, for example, generating a field gradient map. As such, the process 400 can be advantageously faster and less expensive than other processes that require a field gradient map.

An affine function that specifies the difference in shape between the derived three-dimensional tensor to the reference tensor is determined to align the shape of the derived tensor to the shape of the reference tensor 508. For example, an affine factory-function can generate affine functions based on at least two input objects—a source volumetric image and a target volumetric image. The reference tensor may be submitted to the factory-function as the target volumetric image and the derived tensor may be submitted to the factory-function as the source volumetric image. The factory-function can then find an automorphism of an affine space, which maps while preserving affine subspaces of the target and source volumetric images. This automorphism may be recorded as an affine function in computer-readable terms so that computer systems can utilize the affine function to transform an inputted volumetric image.

The affine function is applied to each volumetric image used to derive the derived tensor 510. For example, for each volumetric image in the distorted data, the volumetric image may be submitted to the affine function as an input, and a transformed volumetric image can be supplied as an output. These supplied output volumetric images have each been transformed to reduce or eliminate distortion, and may be compiled into a single 4D image.

In some cases, applying the affine function does not transform a portion of the distorted image data. For example, some portions of the tensor may be minimally transformed or not transformed at all. In many cases, the area of the tensor corresponding to the frontal lobe may be most impacted by the transformation, but areas corresponding to other areas far away from the frontal lobe may be minimally transformed or not transformed at all.

A portion of the derived tensor is selected as an anchor 512. For example, a center of brain-area of the derived tensor (e.g., center of mass, center of geometry) may be found by a center-finding function that receives the derived tensor as an input and provides a voxel location (e.g., in [X,Y,Z] format). This returned voxel location may be used as the anchor of the derived tensor.

A target portion of the reference tensor that corresponds to the anchor is selected 514. For example, a center of the brain area of the derived tensor (e.g., center of mass, center of geometry) may be found by a center-finding function that receives the reference tensor as an input and provides a voxel location (e.g., in [X,Y,Z] format). This returned voxel location may be used as the anchor of the reference tensor.

A translation of the anchor to the target portion is found that minimizes a difference function between the anchor and the target portion 516. For example, the anchor and target portion may be supplied to a translation-solver function that receives these two data objects as input and that returns a translation matrix that specifies a translation to minimize the difference between the two. This may be thought of as "aligning" the anchor and target portion in space without changing the shape of either object. The translation matrix may describe, for example, movement in three dimensions and rotations about the three dimensions.

The translation is applied to each transformed volumetric image 518. For example, each voxel value of each transformed volumetric image may be translated according to the translation matrix found previously. As such, each brain represented by each of the transformed volumetric images may be aligned with the reference tensor. This can result in a final product that is transformed (reshaped to reduce or remove distortion) and translated (moved and/or rotated) to match the shape and orientation of the reference tensor.

Figure 6:
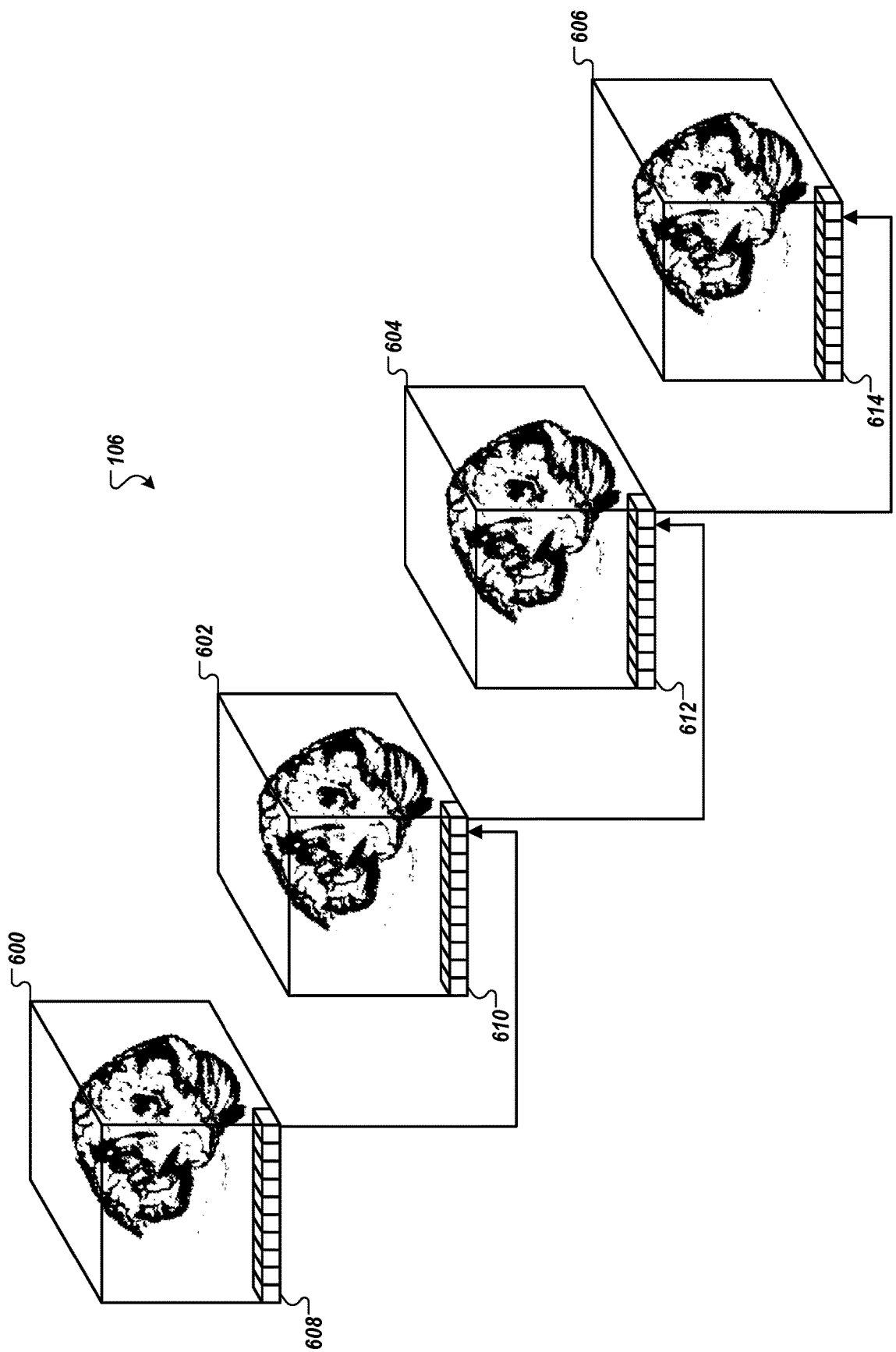
FIG. 6 shows data generated by medical imaging.

FIG. 6 shows data 106 generated by medical imaging. The data 106 may be generated, stored in computer memory, transmitted across computer networks, e.g., in binary format. The data 106 can include a plurality of volumetric images 600-606 (more or fewer are possible) that each represent a scan of a brain at a particular timestamp or within a particular timeframe. The particular format of the scan, and the phenomena being recorded, can vary depending on the type of scan being performed. For example, the data 106 may record the results of a functional magnetic resonance imaging (fMRI) or diffusion tractography.

Each volumetric image 600-606 can incorporate a three-dimensional array of voxels. For clarity, only a single row of voxels 608-614 are shown, but it will be understood that the entirety of the volumetric images 600-606 may be composed of voxels. Each voxel can store one or more values to represent the phenomena being scanned at the corresponding space within or around the patient being scanned. These values may be rendered onto a screen to make a visual representation of the data 106, or may be used in calculations, for example, to aid clinicians in making diagnoses or for other clinical purposes.

The voxels 608-614 can each be uniquely addressed within their volumetric images using the same scheme. For example, each voxel may have an address [X,Y,Z] that identifies the voxel's location in the X, Y, and Z direction from an origin point (e.g., a corner of the volumetric image). By using the same scheme for each volumetric image 200-206, voxels in the same locations in their respective volumetric image may have the same address. As shown here, the voxels in the lower right corner of each volumetric image 200-206 may have the same address (e.g., [9,0,0]). In some cases, the average voxel values each address location across a plurality of volumetric images of the distorted image data 106 may be found. In such a case, each voxel at the same address (e.g., [9,0,0]) may be included in the average. This may be used, for example, when deriving a 3D tensor from the image data 106.

Figure 7:
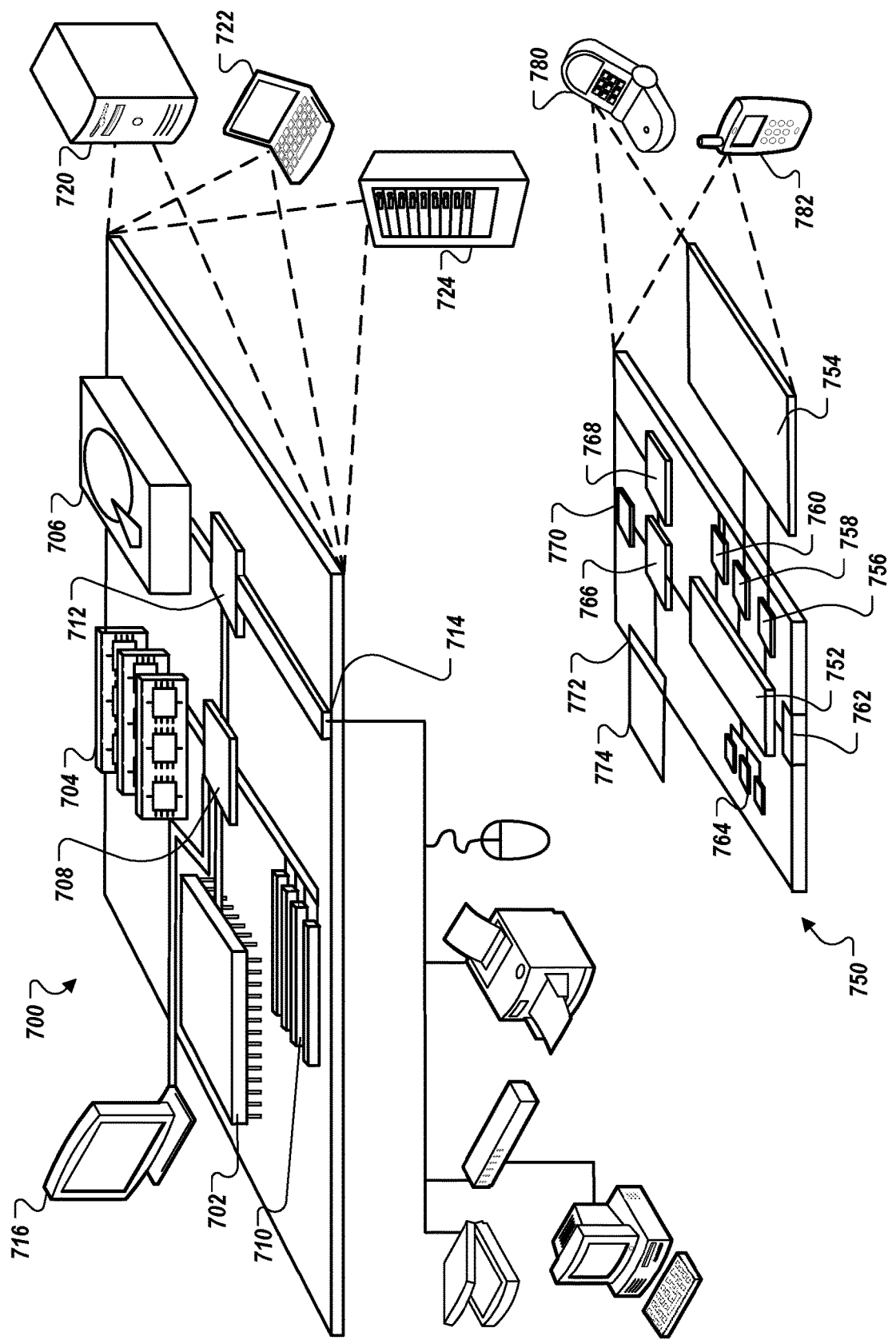
FIG. 7 is a schematic diagram that shows an example of a computing device and a mobile computing device.

FIG. 7 shows an example of a computing device 700 and an example of a mobile computing device that can be used to implement the techniques described here. The computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 can also be another form of computer-readable medium, such as a magnetic or optical disk.

The storage device 706 is capable of providing mass storage for the computing device 700. In some implementations, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. In some implementations, the high-speed interface 708 is coupled to the memory 704, the display 716 (e.g., through a graphics processor or accelerator), and to the high-speed expansion ports 710, which can accept various expansion cards (not shown). In the implementation, the low-speed interface 712 is coupled to the storage device 706 and the low-speed expansion port 714. The low-speed expansion port 714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. In addition, it can be implemented in a personal computer such as a laptop computer 722. It can also be implemented as part of a rack server system 724. Alternatively, components from the computing device 700 can be combined with other components in a mobile device (not shown), such as a mobile computing device 750. Each of such devices can contain one or more of the computing device 700 and the mobile computing device 750, and an entire system can be made up of multiple computing devices communicating with each other.

The mobile computing device 750 includes a processor 752, a memory 764, an input/output device such as a display 754, a communication interface 766, and a transceiver 768, among other components. The mobile computing device 750 can also be provided with a storage device, such as a micro-drive or other device, to provide additional storage. Each of the processor 752, the memory 764, the display 754, the communication interface 766, and the transceiver 768, are interconnected using various buses, and several of the components can be mounted on a common motherboard or in other manners as appropriate.

The processor 752 can execute instructions within the mobile computing device 750, including instructions stored in the memory 764. The processor 752 can be implemented as a chipset of chips that include separate and multiple analog and digital processors. The processor 752 can provide, for example, for coordination of the other components of the mobile computing device 750, such as control of user interfaces, applications run by the mobile computing device 750, and wireless communication by the mobile computing device 750.

The processor 752 can communicate with a user through a control interface 758 and a display interface 756 coupled to the display 754. The display 754 can be, for example, a TFT (Thin-Film-Transistor Liquid Crystal Display) display or an OLED (Organic Light Emitting Diode) display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can provide communication with the processor 752, so as to enable near area communication of the mobile computing device 750 with other devices. The external interface 762 can provide, for example, for wired communication in some implementations, or for wireless communication in other implementations, and multiple interfaces can also be used.

The memory 764 stores information within the mobile computing device 750. The memory 764 can be implemented as one or more of a computer-readable medium or media, a volatile memory unit or units, or a non-volatile memory unit or units. An expansion memory 774 can also be provided and connected to the mobile computing device 750 through an expansion interface 772, which can include, for example, a SIMM (Single In Line Memory Module) card interface. The expansion memory 774 can provide extra storage space for the mobile computing device 750, or can also store applications or other information for the mobile computing device 750. Specifically, the expansion memory 774 can include instructions to carry out or supplement the processes described above, and can include secure information also. Thus, for example, the expansion memory 774 can be provide as a security module for the mobile computing device 750, and can be programmed with instructions that permit secure use of the mobile computing device 750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 764, the expansion memory 774, or memory on the processor 752. In some implementations, the computer program product can be received in a propagated signal, for example, over the transceiver 768 or the external interface 762.

The mobile computing device 750 can communicate wirelessly through the communication interface 766, which can include digital signal processing circuitry where necessary. The communication interface 766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 768 using a radio-frequency. In addition, short-range communication can occur, such as using a Bluetooth, WiFi, or other such transceiver (not shown). In addition, a GPS (Global Positioning System) receiver module 770 can provide additional navigation- and location-related wireless data to the mobile computing device 750, which can be used as appropriate by applications running on the mobile computing device 750.

The mobile computing device 750 can also communicate audibly using an audio codec 760, which can receive spoken information from a user and convert it to usable digital information. The audio codec 760 can likewise generate audible sound for a user, such as through a speaker, e.g., in a handset of the mobile computing device 750. Such sound can include sound from voice telephone calls, can include recorded sound (e.g., voice messages, music files, etc.) and can also include sound generated by applications operating on the mobile computing device 750.

The mobile computing device 750 can be implemented in a number of different forms, as shown in the figure. For example, it can be implemented as a cellular telephone 780. It can also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

What is claimed is:

1. A method of generating an image, the method comprising:
    obtaining distorted image data of a subject brain, the distorted image data comprising a time series of three-dimensional image tensors generated at least in part from an echo planar imaging session of the subject brain, wherein distortion of the distorted image data is caused by external factors shifting locations of individual image data;
    deriving a derived three-dimensional tensor from the distorted image data;

determining a non-rigid alignment function to non-rigidly align the derived three-dimensional tensor to a reference tensor producing a non-rigidly aligned derived 3D tensor;

determining a rigid alignment function to rigidly align the non-rigidly aligned derived 3D tensor to the reference tensor; and producing distortion-corrected image data by applying the rigid alignment function and the non-rigid alignment function to the time series of three-dimensional image tensors.

2. The method of claim 1, wherein determining the rigid alignment function comprises:
   selecting a portion of the derived three-dimensional tensor as an anchor;
   finding a target-portion of the reference tensor that corresponds to the anchor; and
   finding a translation of the anchor that minimizes a different function between the anchor and the target portion.

3. The method of claim 2, wherein selecting a portion of the derived three-dimensional tensor as an anchor comprises finding a center of the derived three-dimensional tensor.

4. The method of claim 1, wherein determining the non-rigid alignment function comprises determining an affine transformation that specifies a difference in shape between the derived three-dimensional tensor to the reference tensor.

5. The method of claim 4, wherein the transformation, when applied to the distorted image data, transforms a first portion of the distorted image data and does not transform a second portion of the distorted image data.

6. The method of claim 1, wherein deriving a derived three-dimensional tensor from the distorted image data comprises averaging voxel values of each address location across a plurality of volumetric images of the distorted image data.

7. The method of claim 1, the method further comprising one of the group consisting of i) displaying the distortion-corrected image data to a user; ii) storing the distortion-corrected image data; and iii) performing clinical analysis for the subject brain using the distortion-corrected image to produce a result different than what would be produced performing the clinical analysis on the distorted image data.

8. The method of claim 1, wherein the echo planar imaging session of the subject brain is free of a sensing for generation of a field gradient map and wherein the producing of the distortion-corrected image data is performed free of a field gradient map.

9. The method of claim 1, wherein the echo planar imaging is one of the group consisting of functional magnetic resonance (fMRI) and imaging and diffusion tractography (DT).

10. The method of claim 1, wherein the reference tensor represents a T1 image.

11. A system for generating an image, the system comprising:
    one or more computers and one or more storage devices on which are stored instructions that are operable, when executed by the one or more computers, to cause the one or more computers to perform operations comprising:
      obtaining distorted image data of a subject brain, the distorted image data comprising a time series of three-dimensional image tensors generated at least in part from an echo planar imaging session of the subject brain, wherein distortion of the distorted image data is caused by external factors shifting locations of individual image data;
      deriving a derived three-dimensional tensor from the distorted image data;
      determining a non-rigid alignment function to non-rigidly align the derived three-dimensional tensor to a reference tensor producing a non-rigidly aligned derived 3D tensor;
      determining a rigid alignment function to rigidly align the non-rigidly aligned derived 3D tensor to the reference tensor; and
      producing distortion-corrected image data by applying the rigid alignment function and the non-rigid alignment function to the time series of three-dimensional image tensors.

12. The system of claim 11, wherein determining the rigid alignment function comprises:
    selecting a portion of the derived three-dimensional tensor as an anchor;
    finding a target-portion of the reference tensor that corresponds to the anchor; and
    finding a translation of the anchor that minimizes a different function between the anchor and the target portion.

13. The system of claim 12, wherein selecting a portion of the derived three-dimensional tensor as an anchor comprises finding a center of the derived three-dimensional tensor.

14. The system of claim 11, wherein determining the non-rigid alignment function comprises determining an affine transformation that specifies a difference in shape between the derived three-dimensional tensor to the reference tensor.

15. The system of claim 14, wherein the transformation, when applied to the distorted image data, transforms a first portion of the distorted image data and does not transform a second portion of the distorted image data.

16. The system of claim 11, wherein deriving a derived three-dimensional tensor from the distorted image data comprises averaging voxel values of each address location across a plurality of volumetric images of the distorted image data.

17. The system of claim 11, the operations further comprising one of the group consisting of i) displaying the distortion-corrected image data to a user; ii) storing the distortion-corrected image data; and iii) performing clinical analysis for the subject brain using the distortion-corrected image to produce a result different than what would be produced performing the clinical analysis on the distorted image data.

18. The system of claim 11, wherein the echo planar imaging session of the subject brain is free of a sensing for generation of a field gradient map and where the producing of the image data is performed free of a field gradient map.

19. The system of claim 11, wherein the echo planar imaging is one of the group consisting of functional magnetic resonance (fMRI) and imaging and diffusion tractography (DT).

20. The system of claim 11, wherein the reference tensor represents a T1 image.

21. The method of claim 1, wherein the distorted image data contains shifted locations of intensity values without changes to those intensity values.

22. The method of claim 1, wherein air in a sinus cavity of the subject influences the echo planar imaging session resulted in the distortion of the distorted image data.

23. The system of claim 11, wherein the distorted image data contains shifted locations of intensity values without changes to those intensity values.

24. The system of claim 11, wherein air in a sinus cavity of the subject influences the echo planar imaging session resulted in the distortion of the distorted image data.

* * * * *